US006458362B1

(12) United States Patent
Casal et al.

(10) Patent No.: US 6,458,362 B1
(45) Date of Patent: Oct. 1, 2002

(54) RECOMBINANT VP2 PARVOVIRAL PSEUDO-PARTICLES ENCODING CTL OR T-HELPER CELL EPITOPES

(75) Inventors: Ignacio Casal, Madrid (ES); Christine Sedlik, Argenteuil (FR); Javier Sarraseca, Madrid (ES); Richard Lo-Man, Paris (FR); Paloma Rueda, Madrid (ES); Claude Leclerc, Paris (FR)

(73) Assignees: Institut Pasteur, Paris (FR); Immunologia Y Genetica Aplicada S.A., Madrid (ES)

( * ) Notice: Subject to any disclaimer, the term of this patent is extended or adjusted under 35 U.S.C. 154(b) by 0 days.

(21) Appl. No.: 08/704,867

(22) Filed: Aug. 30, 1996

(30) Foreign Application Priority Data

Jan. 2, 1996 (EP) .......................................... 96 400 009

(51) Int. Cl.[7] ............................................... A61K 39/12
(52) U.S. Cl. ................................ 424/199.1; 435/235.1; 435/320.1; 424/184.1; 424/186.1; 424/192.1; 424/233.1
(58) Field of Search .................................. 530/403, 424, 530/196.11; 424/93.2; 435/235.1

(56) References Cited

FOREIGN PATENT DOCUMENTS

WO        WO 91/04330      *    4/1991

OTHER PUBLICATIONS

Brown C. et al., Chimeric parvovirus B19 capsides for the presentation of foreign epitopes Virol. 198:477–488, Feb. 1994.*

Niedermann et al., "Contribution of proteasome–mediated proteolysis to the hierarchy of epitopes presented by major histocompatibility complex class I molecules.", Immunity, (Mar. 1995) 2(3):289–99.*

Yellen–Shaw et al., Point mutation flanking a CTL epitope ablates in vitro and in vivo recognition of a full–length viral protein. Journal of Immunology, (Apr. 1, 1997) 158(7):3227–34.*

Lo–Man et al., "Molecular context of a viral T cell determinant within a chimeric bacterial protein alters the diversity of its T cell recognition,", Journal of Immunology, (Jun. 15 1994) 152 (12):5660–9.*

Leclerc et al., "Immunodominance of a recombinant T–cell epitode depends on its molecular environment.", Moledular Immunology, (Dec. 1993) 30(17):1561–72.*

Christine Sedlik et al., "Immunogenicity of Polovirus B and T Cell Epitopes Presented By Hybrid Porcine Parvovirus Particles", Journal of General Virology, vol. 76, pp. 2361–2368, 1995.*

Koichi Miyamura et al., "Parvovirus Particles as Platforms For Protein Presentation", Proc. Natl. Acad. Sci. USA, vol. 91, pp. 8507–7511, Aug. 1994.*

Demetrius Moskophidis et al., "Immunobiology of Cytotoxic T–Cell Escape Mutants of Lymphocytic Choriomeningitis Virus", Journal of virology, vol. 69, No. 4, pp. 2187–2193, Apr. 1995.*

* cited by examiner

Primary Examiner—Laurie Scheiner
Assistant Examiner—Jeffrey S. Parkin
(74) Attorney, Agent, or Firm—Oblon, Spivak, McClelland, Maier & Neustadt, P.C.

(57) ABSTRACT

Attempts to generate modified viral pseudo-particles that are capable of stably incorporating heterologous antigenic determinants has encountered a number of difficulties including inhibition of pseudo-particle formation following epitope insertion and failure of the epitope to retain its native configuration. The present invention is directed toward recombinant viral pseudo-particles of the family Parvoviridae that stably encode heterologous epitopes. Hybrid virus-like particles (VLP) were prepared by self-assembly of a modified porcine parvovirus (PPV) VP2 capsid protein carrying a CD8[+] or CD4[+] T cell epitope in the amino terminus. Immunization of mice with hybrid pseudo-particles carrying a lymphocytic choriomeningitis virus (LCMV) nucleoprotein CTL epitope, without adjuvant, induced strong cytotoxic T lymphocyte (CTL) responses against both peptide-coated- or virus-infected-target cells. Immunization of mice with hybrid pseudo-particles carrying a hepatitis B virus (HBV) T helper cell epitope, without adjuvant, induced strong T helper lymphocyte responses against the reporter epitope. These recombinant viral pseudo-particles are easily produced by the baculovirus expression system and, therefore, represent a promising and safe strategy to induce strong CTL and T-helper cell responses for the elimination of virus-infected cells.

14 Claims, 11 Drawing Sheets

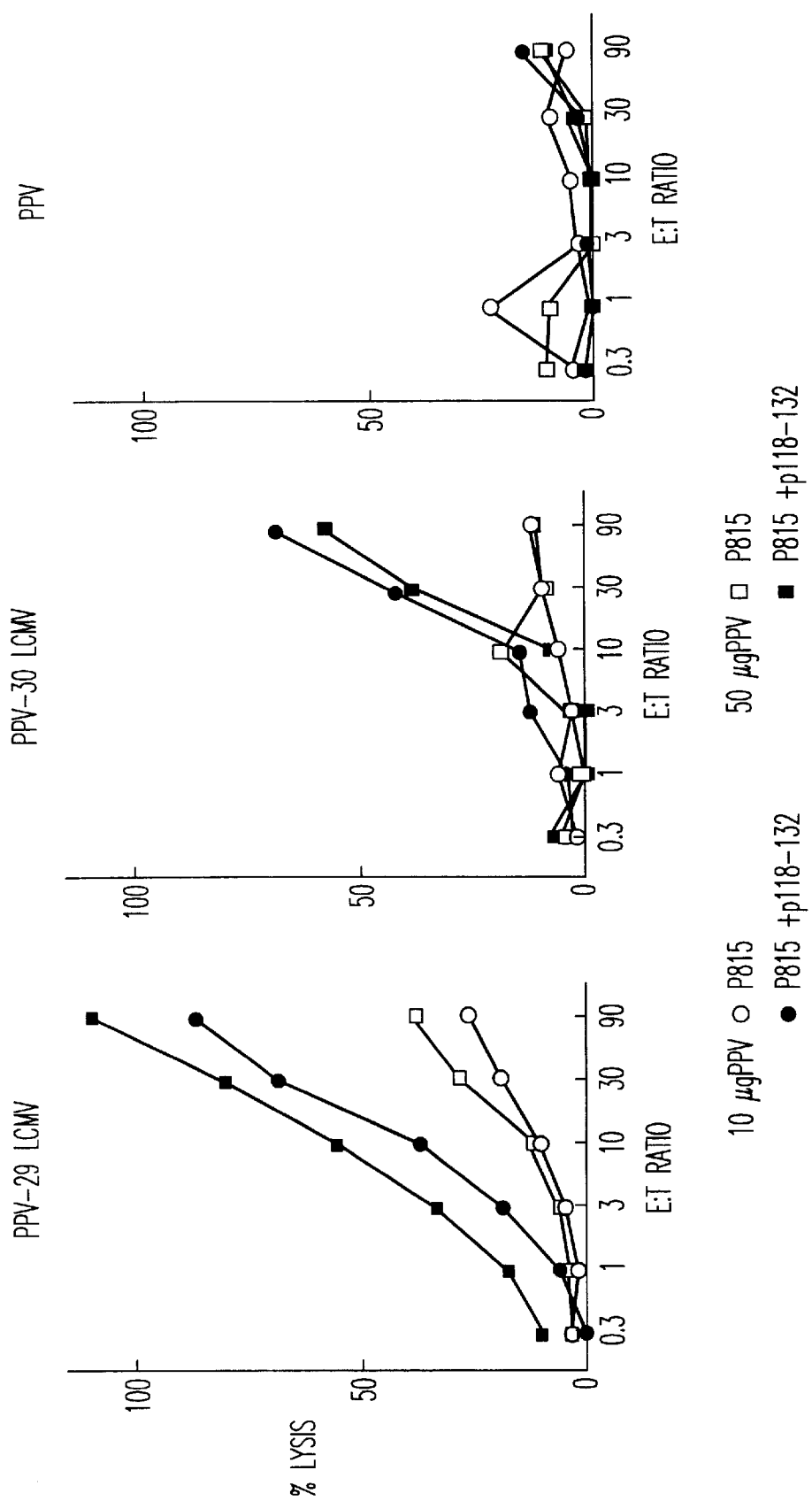

50 µgPPV-30 LCMV

FIG. 3A

10 µgPPV-30 LCMV

FIG. 3B

2 µgPPV-30 LCMV

FIG. 3C

0.4 µgPPV-30 LCMV

FIG. 3D

0.08 µgPPV-30 LCMV

10 µgPPV

FIG. 3F

100 µg118-126+ IFA

FIG. 3G

□ p120-132   ■ PPV-PreS:T   ○ VP2

SEQUENCE LISTING

<160> NUMBER OF SEQ ID NOS: 14

<210> SEQ ID NO 1
<211> LENGTH: 54
<212> TYPE: DNA
<213> ORGANISM: Artificial Sequence
<220> FEATURE:

```
<223> OTHER INFORMATION: synthetic DNA

<400> SEQUENCE: 1
tcgagatgcg accacaagct tcaggagtat acatgggaaa cctaacagca caac        54

<210> SEQ ID NO 2
<211> LENGTH: 54
<212> TYPE: DNA
<213> ORGANISM: Artificial Sequence
<220> FEATURE:
<223> OTHER INFORMATION: synthetic DNA

<400> SEQUENCE: 2
tcgagttgtg ctgttaggtt tcccatgtat actcctgaag cttgtggtcg catc        54

<210> SEQ ID NO 3
<211> LENGTH: 45
<212> TYPE: DNA
<213> ORGANISM: Artificial Sequence
<220> FEATURE:
<223> OTHER INFORMATION: synthetic DNA

<400> SEQUENCE: 3
tcgagatgca atggaattct accaccttcc accaaaccct gcaac                  45

<210> SEQ ID NO 4
<211> LENGTH: 45
<212> TYPE: DNA
<213> ORGANISM: Artificial Sequence
<220> FEATURE:
<223> OTHER INFORMATION: synthetic DNA

<400> SEQUENCE: 4
tcgagttgca gggtttggtg gaaggtggta gaattccatt gcatc                  45

<210> SEQ ID NO 5
<211> LENGTH: 48
<212> TYPE: DNA
<213> ORGANISM: Artificial Sequence
<220> FEATURE:
<223> OTHER INFORMATION: synthetic DNA

<400> SEQUENCE: 5
tcgagatgaa gcttttcgct gtctggaaga tcacctacaa agacaccc               48

<210> SEQ ID NO 6
<211> LENGTH: 48
<212> TYPE: DNA
<213> ORGANISM: Artificial Sequence
<220> FEATURE:
<223> OTHER INFORMATION: synthetic DNA

<400> SEQUENCE: 6
ctacttcgaa aagcgacaga ccttctagtg gatgtttctg tgggagct               48

<210> SEQ ID NO 7
<211> LENGTH: 42
<212> TYPE: DNA
<213> ORGANISM: Artificial Sequence
<220> FEATURE:
<223> OTHER INFORMATION: synthetic DNA

<400> SEQUENCE: 7
tcgagatgga caacccgct agcaccacca acaaggacaa ac                      42
```

-continued

<210> SEQ ID NO 8
<211> LENGTH: 42
<212> TYPE: DNA
<213> ORGANISM: Artificial Sequence
<220> FEATURE:
<223> OTHER INFORMATION: synthetic DNA

<400> SEQUENCE: 8
ctacctgttg gggcgatcgt ggtggttgtt cctgtttgag ct        42

<210> SEQ ID NO 9
<211> LENGTH: 27
<212> TYPE: DNA
<213> ORGANISM: Artificial Sequence
<220> FEATURE:
<223> OTHER INFORMATION: synthetic DNA

<400> SEQUENCE: 9
gcctcaacta gttgtaggaa tatattt        27

<210> SEQ ID NO 10
<211> LENGTH: 27
<212> TYPE: DNA
<213> ORGANISM: Artificial Sequence
<220> FEATURE:
<223> OTHER INFORMATION: synthetic DNA

<400> SEQUENCE: 10
catttaacta gttctcattt ttgctgg        27

<210> SEQ ID NO 11
<211> LENGTH: 27
<212> TYPE: DNA
<213> ORGANISM: Artificial Sequence
<220> FEATURE:
<223> OTHER INFORMATION: synthetic DNA

<400> SEQUENCE: 11
gtttcaacta gttattattc taggttg        27

<210> SEQ ID NO 12
<211> LENGTH: 27
<212> TYPE: DNA
<213> ORGANISM: Artificial Sequence
<220> FEATURE:
<223> OTHER INFORMATION: synthetic DNA

<400> SEQUENCE: 12
ttccatgggt gaaaatgtgg aacaaca        27

<210> SEQ ID NO 13
<211> LENGTH: 33
<212> TYPE: DNA
<213> ORGANISM: Artificial Sequence
<220> FEATURE:
<223> OTHER INFORMATION: synthetic DNA

<400> SEQUENCE: 13
tcgagatgtt cgaacaaaac accgctcaac ccc        33

<210> SEQ ID NO 14
<211> LENGTH: 33
<212> TYPE: DNA

-continued

<213> ORGANISM: Artificial Sequence
<220> FEATURE:
<223> OTHER INFORMATION: synthetic DNA

<400> SEQUENCE: 14
tcgaggggtt gagcggtgtt ttgttcgaac atc       33

RECOMBINANT VP2 PARVOVIRAL PSEUDO-PARTICLES ENCODING CTL OR T-HELPER CELL EPITOPES

The present invention relates to recombinant viral pseudo-particles of a virus of the Parvoviridae family or of a related virus, useful in particular for inducing cytotoxic $CD8^+$ T lymphocyte (CTL) and $CD4^+$ helper T lymphocyte responses in vivo at a high level.

Another object is the use of these pseudo-particles for the production of antitumoral vaccines or drugs.

It also covers compositions comprising said pseudo-particles in a physiologically acceptable excipient and/or diluent.

According to Fernandez et al. (Médecine/Sciences, 1995, 11, 975–983), the response to cellular mediation, essential in the case of a tumor, can be divided into two parts:
on the one hand the initiation of the response which causes the involvement of the $CD4^+$ T lymphocytes and the cells presenting the antigen (CPA), and
on the other hand the cytotoxic effector response in which the $CD8^+$ T lymphocytes are involved.

The activated $CD4^+$ T lymphocytes proliferate and secrete cytokines while the activated $CD8^+$ T lymphocytes proliferate and differentiate into cytotoxic T lymphocytes (CTL).

These two families of lymphocytes thus have very different functions and are activated by distinct mechanisms. The stimulation of the $CD4^+$ Lymphocytes requires the association of a peptide arising from the degradation of the antigen to class II molecules of the Major Histocompatibility Complex (MHC), while those of the $CD8^+$ cells require the association of a peptide to class I molecules of the MHC.

A number of prophylactic or therapeutic strategies have already been proposed in attempts to control various human and animal diseases caused by viruses, bacteria, parasites, or cancerous or tumoral diseases.

For example, the induction of CTL responses in vivo by "live" vectors is known. However, the safety of these vectors is not guaranteed, particularly towards immunocompromised individuals. In addition, the systems using the replication of these "live" vectors do not retain their activity in immune individuals.

Martinez et al., teach in Vaccine (vol. 10, pp. 684–690, 1992) the use of empty capsids of pig parvovirus (PPV) in pig vaccination. The Parvoviridae family contains viruses very widely distributed in mammals such as pigs, cattle, cats, rabbits, rats and man. However, the parvoviruses are relatively specific to their host mammals. Pig parvovirus (PPV), in particular, is responsible for many infections in industrial pig breeding. Pig parvovirus (PPV) is composed of a non-enveloped isometric particle of diameter 20 nm with icosahedral symmetry, containing a single-strand DNA molecule. It is composed of two capsid proteins, VP1 (83 kDa) and VP2 (64 kDa), and a third protein, VP3, resulting from the proteolysis of VP2.

The VP2 protein can be produced by insect cells using a recombinant baculovirus system, and the VP2 proteins produced are capable of auto-assembly to form viral pseudo-particles which have the same size as the native virion. The vaccination of pigs against PPV is performed by immunizing them with a mixture of said capsids in combination with the adjuvant Alhydrogel (50%) +Quil A 500 µg (Superfos). A comparable teaching to that of this article is found in applications EP-551.449 and EP-554.414, which also disclose that antigenic determinants corresponding to other viral proteins may be incorporated into the capsids, without however specifying the nature of these antigenic determinants.

Application EP-647.655 relates to synthetic peptides corresponding to the antigenic sites of VP2. It thus does not describe the complete protein.

Attempts to modify the pseudo-particles with a view to incorporating heterologous antigenic determinants come up against difficulties such as the inhibition of the formation of the pseudo-particles. Even when the latter are formed, the heterologous antigenic determinant is not necessarily immunogenic; the antigenic determinant for example may be located in a site where it is incapable of taking up its natural conformation, or of being produced by the cells presenting the antigen.

In other respects, in the same way as vaccines with "live" vectors, the safety of these hybrid particles combined with adjuvants is not completely guaranteed, since a toxicity may arise from some properties of the adjuvants able to induce secondary effects which are harmful to the organism.

It is thus apparent from the state of the art that there is no known reliable and effective system for stimulating the cytotoxic T-lymphocyte response and or cytokine secretion, without risk to the health of the individual treated and without use of immunostimulant adjuvants.

The applicant has shown that it is possible to induce specifically a $CD8^+$ lymphocyte response, in other words a cytotoxic response, and/or a cytokine secretion by the $CD4^+$ T cells, using pseudo-particles containing antigenic determinants able to associate with at least one class I or class II molecule, respectively, of the MHC.

The object of the present invention is recombinant viral pseudo-particles produced by auto-assembly of at least one viral structural protein, having a size of between 20 and 60 nm and forming an approximately icosahedral structure, said protein being modified by the presence of at least one antigenic determinant comprising a sequence of 8 to 25 amino acids, able to associate with at least one class I or II molecule of the major histocompatibility complex (MHC), or of a combination of several of these antigenic determinants.

The $CD8^+$ T lymphocytes according to the invention are able to recognize at least one antigenic determinant comprising a sequence of 8 to 9 amino acids able to associate with at least one class I MHC molecule.

The $CD4^+$ T lymphocytes according to the invention are able to recognize at least one antigenic determinant comprising a sequence of between 8 and 25 amino acids able to associate with at least one class II MHC molecule.

Advantageously, the structural proteins comprise at least one parvovirus protein of the Parvoviridae family, or of a related virus, and preferentially at least one VP2 protein.

The particles according to the invention may also be particles composed of surface or core proteins of the hepatitis B virus, particles of poliovirus, of rabbit hemorrhagic virus, of Norwalk virus, of rotavirus, of retrovirus gag proteins (HIV, FIV, FeLV) or, in general, particles of any non-enveloped virus able to auto-assemble in vitro by the expression of one or more viral proteins.

The particles according to the invention may comprise proteins of various types, and form hybrid particles. They may for example be composed of VP1 and VP2 proteins.

The association formed between the amino acid sequence comprising the antigenic determinant and the class I and/or II molecules is recognized by the $CD8^+$ or $CD4^+$ T lymphocyte receptor and induces a differentiation and proliferation of these lymphocytes.

Advantageously, said sequence is bounded by regions known as flanking regions able to modulate its degradation, in other words to facilitate its production during the degradation of the antigen, or to facilitate its binding to class I or II MHC molecules.

The flanking regions may correspond to amino acids flanking the CD8+ or CD4+ T antigenic determinant in its natural environment. In general, they may be composed of several amino acids, and in particular alanine or lysine.

The pseudo-particles according to the invention have a first advantage, arising from the safety of this method of immunization, the vector used being non-replicating, consisting of a single type of viral protein and being able to be administered even to immunocompromised individuals.

A second advantage of the pseudo-particles according to the invention lies in the absence of cross-reactions with human parvovirus and thus in the absence of problems associated with a pre-immunization of the individuals, possibly leading to a weak immunogenicity of this type of recombinant vaccine.

In addition the pseudo-particles according to the invention do not require the replication of the vector and should thus retain their effectiveness in immune individuals.

Also, the pseudo-particles according to the invention have an excellent immunogenicity—only a single immunization is needed—and can thus be used in the absence of an immunostimulant adjuvant.

The parvovirus is advantageously PPV, CPV (Canine Parvovirus), or another related virus such as FPLV (Feline Panleukopenia virus) or MEV (Mink Enteritis virus).

The antigenic determinant may be composed of any sequence binding to a class I MHC molecule and able to induce a T lymphocyte cytotoxicity. It may also be composed of a sequence binding to a class II molecule in which case it is able to induce a helper response and/or cytokine production. It may in particular be a CD8+ T antigenic determinant of a virus, such as HIV-1 or HIV-2, or influenza virus, or a tumoral antigenic determinant or one expressed by cancer cells.

According to an advantageous embodiment, the pseudo-particles according to the invention are characterized in that the selected antigenic determinant is the CD8+ CTL antigenic determinant contained in the 118–132 region of the nucleoprotein of lymphocytic choriomeningitis virus (LCMV).

The antigenic determinant may however be any other antigenic determinant able to induce a CTL response, such as for example one of the following antigenic determinants:

The antigenic determinants of the Env gp120, Env gp41, Gag p17, Gag p24, Gag p15, Pol and Nef proteins of the HIV virus, and the antigenic determinants of the Gag and nef proteins of the SIV virus and the Gag protein of the HIV-2 virus, as defined by Venet and Walker (AIDS 1993, Vol. 7, suppl. 1, 119–120).

The antigenic determinants of the proteins expressed by tumors which develop in man, such as the proteins expressed by the MAGE-1, MAGE-3, BAGE, GAGE-1,2, HER-2/neu genes, and melanocytic differentiation antigens, such as tyrosinase, Pmel17gp100, Melan-AMART-1, and gp75TRP1, defined by Van Den Eynde and Brichard (Current Opinion in Immunology, 1995, 7, 674–681).

The antigenic determinant may also be an antigenic determinant able to induce a CD4+ helper T response, such as for example one of the following antigenic determinants:

The antigenic determinants expressed by viruses such as poliovirus, for example the $C_3$:T antigenic determinant of the $PV_1$ poliovirus contained in the 103–115 region, or the viral hepatitis virus, such as the PreS:T antigenic determinant contained in the PreS2 120–132 region of the hepatitis B virus.

The pseudo-particle may also comprise a combination of antigenic determinants, and in particular:

at least one CD4+ T antigenic determinant and at least one CD8+ T antigenic determinant a combination of multicopies of CD4+ or CD8+ T antigenic determinants a combination of four copies of the Mut CD8+ T antigenic determinants of Lewis carcinoma.

By a combination of antigenic determinants should be understood a combination comprising at least two antigenic determinants and preferably between two and ten antigenic determinants of identical proteins, such as for example a multicopy of the Mut 1 antigenic determinants of Lewis carcinoma, or of different proteins. Thus a combination of multicopies of CD8+ T antigenic determinants may comprise at least two antigenic determinants and preferably between two and ten antigenic determinants originating from different proteins, such as the combination of a CD8+ T antigenic determinant of the nucleoprotein of lymphocytic choriomeningitis virus and an Env gp 41 CD8+ T antigenic determinant of HIV.

Said recombinant viral pseudo-particles may advantageously be obtained by a process comprising a step of expression in a baculovirus of the chimeric protein consisting of the VP2 protein and said antigenic determinant.

The pseudo-particles according to the invention are obtained, even more preferably, by auto-assembly of the parvovirus VP2 protein modified by the presence, at its N-terminal end, of at least one antigenic determinant of the LCMV nucleoprotein or of at least one antigenic determinant of HBV, poliovirus, or a combination of multicopies of antigenic determinants.

It should be noted that any other molecule, and in particular any other protein, with properties similar to those of VP2, such as auto-assembly, and able to be modified by an antigenic determinant, may be used within the scope of the present invention instead of VP2.

Another object of the present invention is the use of the pseudo-particles in an effective quantity for immunization, to induce CTL and/or CD4+ helper T responses in vivo at a high level.

By the expression "effective quantity for immunization" should be understood a quantity of the pseudo-particles according to the invention chosen as a function of the administration route and of the weight of the individual. The quantity administered is advantageously between 10 and 500 $\mu$g of pseudo-particles per individual.

A further object of the present invention is a composition comprising the pseudo-particles in an immunologically excipient and/or diluent from the immunological point of view. As diluent may be used an aqueous solution buffered to around pH 7 (physiological solution).

Advantageously, the composition according to the present invention is free from immunostimulant adjuvant. It may nevertheless contain, if necessary, such an adjuvant which may be aluminum hydroxide.

The pseudo-particles according to the present invention may also be used in an in vitro stimulation process of the cytotoxic T responses of lymphocytes originating from subjects suffering from viral or tumoral infections, comprising bringing the subjects' lymphocytes into contact with the pseudo-particles. In this case, the cells are, after treatment, readministered to the patients, for example by injection.

Another object of the present invention is the use of the pseudo-particles according to the invention in the preparation of a vaccine, preferably a single-dose vaccine, and in particular antitumoral or antiviral. It may be administered by normal routes for vaccines, i.e. via intramuscular, intradermal, subcutaneous or possibly oral routes, or any other route leading to a CTL and/or CD4+ T response.

The invention will be illustrated, without in any way being limited by, the following description, made with reference to the attached drawings in which:

FIG. 1 represents the process for obtaining the pPPV 29 plasmid.

FIG. 2, comprising three FIGS. 2(a), 2(b) and 2(c), illustrates the immunization of mice, in two stages, at d0 and d21 with respectively 10 and 50 μg of pseudo-particles according to the invention, without adjuvant. At d28, the splenocytes were stimulated in vitro for 5 days with syngeneic splenocytes pre-incubated with synthetic peptide 118–132. The cytotoxic T lymphocyte activity was measured on P815 targets pre-incubated with medium or with synthetic peptide 118–132. The results are expressed in % of lysis, with the ratio E:T as the abscissa, this expression E/T designating the ratio of effector lymphocytes/target cells. FIG. 2(a) shows the results obtained with particle PPV-29 LCMV, FIG. 2(b) the results obtained with particle PPV-30 LCMV and FIG. 2(c) for comparison with unmodified pseudo-particles.

FIG. 3, comprising 7 FIGS., 3(a), 3(b), 3(c), 3(d), 3(e), 3(f) and 3(g), illustrates the immunization of mice, in two stages, at d0 and d21 with different doses respectively of 50 μg for FIG. 3(a), 10 μg for FIG. 3(b), 2 μg for FIG. 3(c), 0.4 μg for FIG. 3(d), and 0.08 μg for FIG. 3(e) of pseudo-particles according to the invention, without adjuvant. At d28, the splenocytes were stimulated in vitro for 5 days with syngeneic splenocytes pre-incubated with synthetic peptide 118–132. The cytotoxic T lymphocyte activity was measured on P815 targets pre-incubated with medium or with synthetic peptide 118–132. The control mice received an injection at d21 of 100 μg of synthetic peptide 118–126 in incomplete Freund's adjuvant (IFA) (FIG. 3g) or control pseudo-particles (FIG. 3f). The results are expressed in % of lysis, in the same way as for FIG. 2.

FIG. 4 comprises, similarly to FIG. 2, three FIGS. 4(a), 4(b) and 4(c), illustrating the immunization of mice by a single injection of 10 μg or of 50 μg of pseudo-particles according to the invention, without adjuvant. At d14, the splenocytes were stimulated in vitro for 5 days with syngeneic splenocytes pre-incubated with synthetic peptide 118–132. The cytotoxic T lymphocyte activity was measured on P815 targets pre-incubated with medium or with synthetic peptide 118–132. The results are expressed in % of lysis, in the same way as for FIG. 2.

FIG. 5, comprising two FIGS. 5(a) and 5(b), illustrates the protection of BALB/c mice, injected intraperitoneally (i.p.) at days 0 and 21 with PBS, or with empty pseudo-particles (PPV) or expressing the sequence 118–132 of the LCMV nucleoprotein (PPV-LCMV), or with Armstrong-strain virus (LCMV-Arms), against infection by LCMV respectively at days 28 (5a) and 70 (5b). The mice were infected intracerebrally with $10^{1.7}$ PFU/mouse. The mortality of the mice was followed daily and the results are expressed in % survival among the animals in each batch.

Figure 10A:
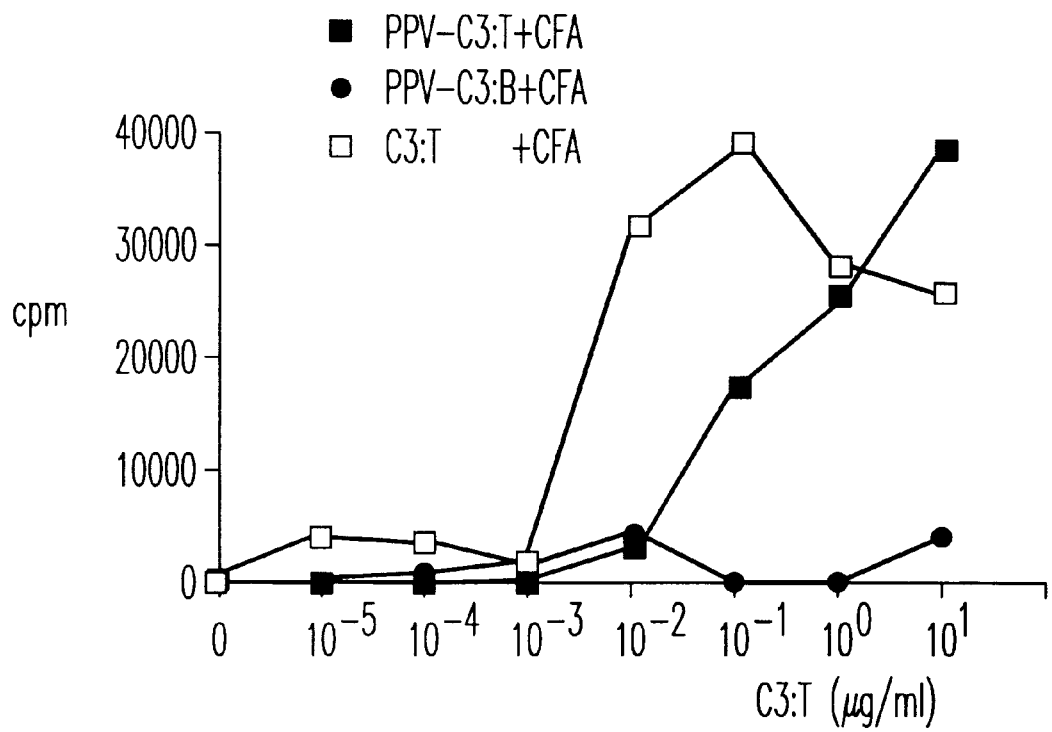
Figure 10B:
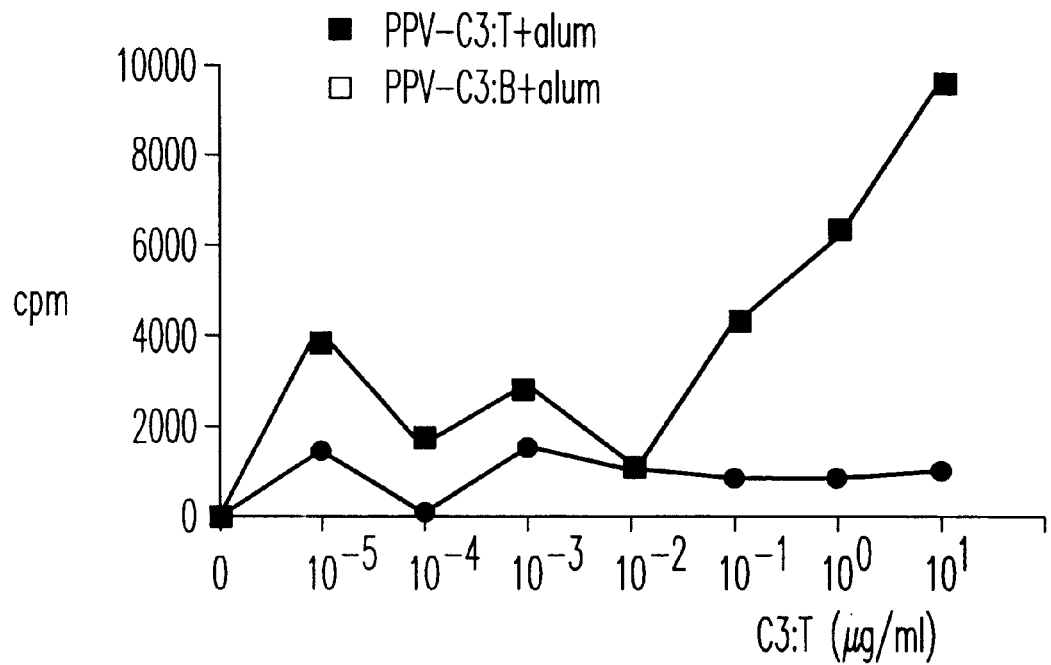

FIGS. 10A and 10B illustrate the in vivo induction of the proliferative T cell response by the C3:T antigenic determinant expressed in PPV pseudo-particles. 10 μg of antigen (PPV C3:T or PPV C3:B or the synthetic peptide C3:T) were subcutaneously injected into BALB/c mice in the presence of complete Freund's adjuvant (CFA) (FIG. 10A) or intraperitoneally with 1 mg of aluminum hydroxide (FIG. 10B). After two weeks, the lymphatic ganglion (FIG. 10A) or spleen cells (FIG. 10B) were restimulated in vitro by different doses of peptide C3:T. The cell proliferation was measured by the incorporation of tritiated thymidine during the final eighteen hours of culture.

EXAMPLE 1

Induction of T Lymphocyte Cytotoxicity by the Pseudo-Particles According to the Invention Containing an LCMV Nucleoprotein Antigenic Determinant.

The heterologous CD8+ CTL antigenic determinant contained in the 118–132 region of the LCMV nucleoprotein was introduced into the PPV VP2 gene without altering the subsequent formation of the pseudo-particles. Two particles were obtained, PPV-29 LCMV and PPV-30 LCMV, differing only in their initiation codon. These chimeric proteins were produced by a baculovirus system and purified by precipitation with ammonium sulfate from the lysate of insect cells according to the procedure described in Journal of General Virology 76: pp. 2361–2368 (1995).

The capacity of these recombinant particles to induce cytotoxic T lymphocyte responses was analyzed in vivo in BALB/c mice.

Materials and methods

Insertion of the LCMV CD8+ antigenic determinant into the XhoI site of the N-terminal end of VP2.

Figure 1:
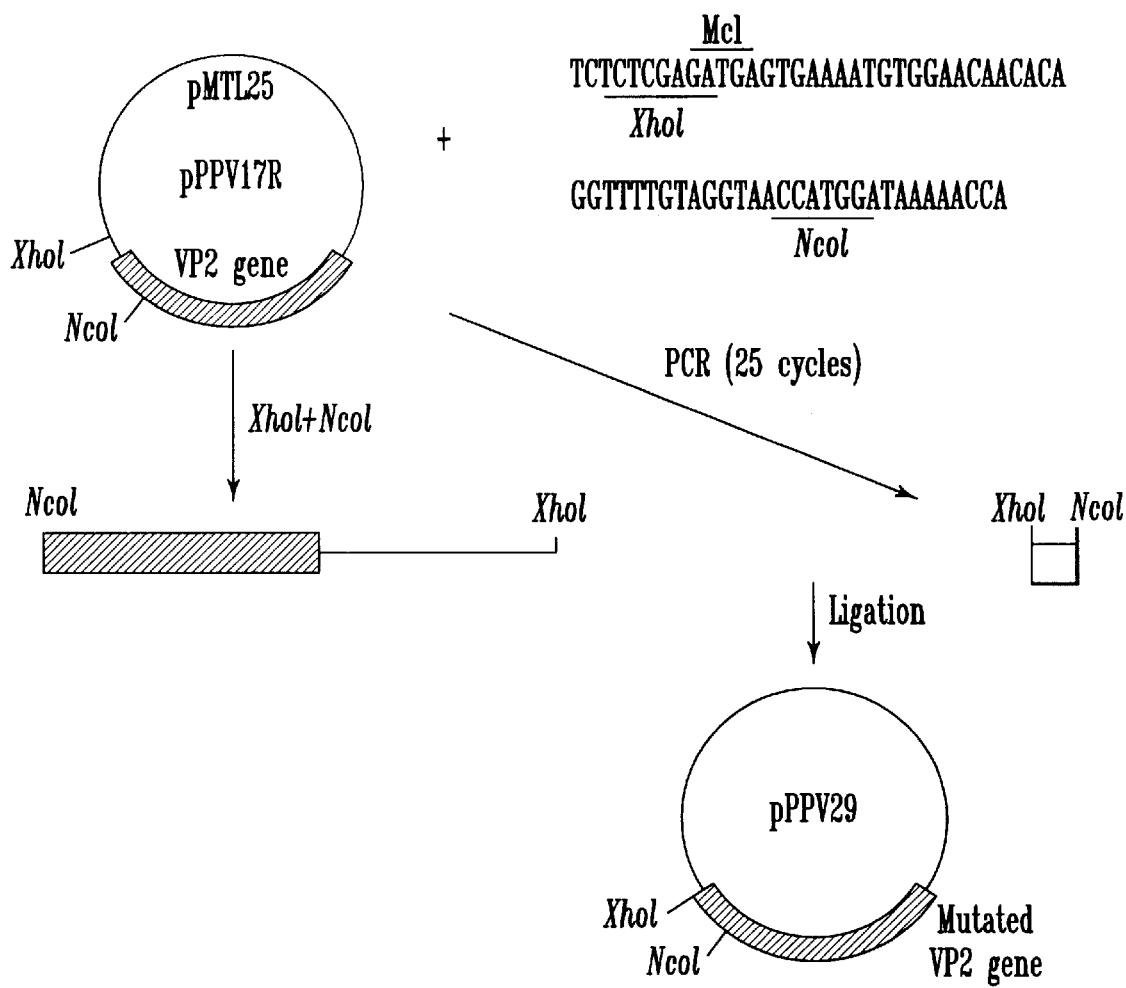
Figures 4A, 4B, 4C:
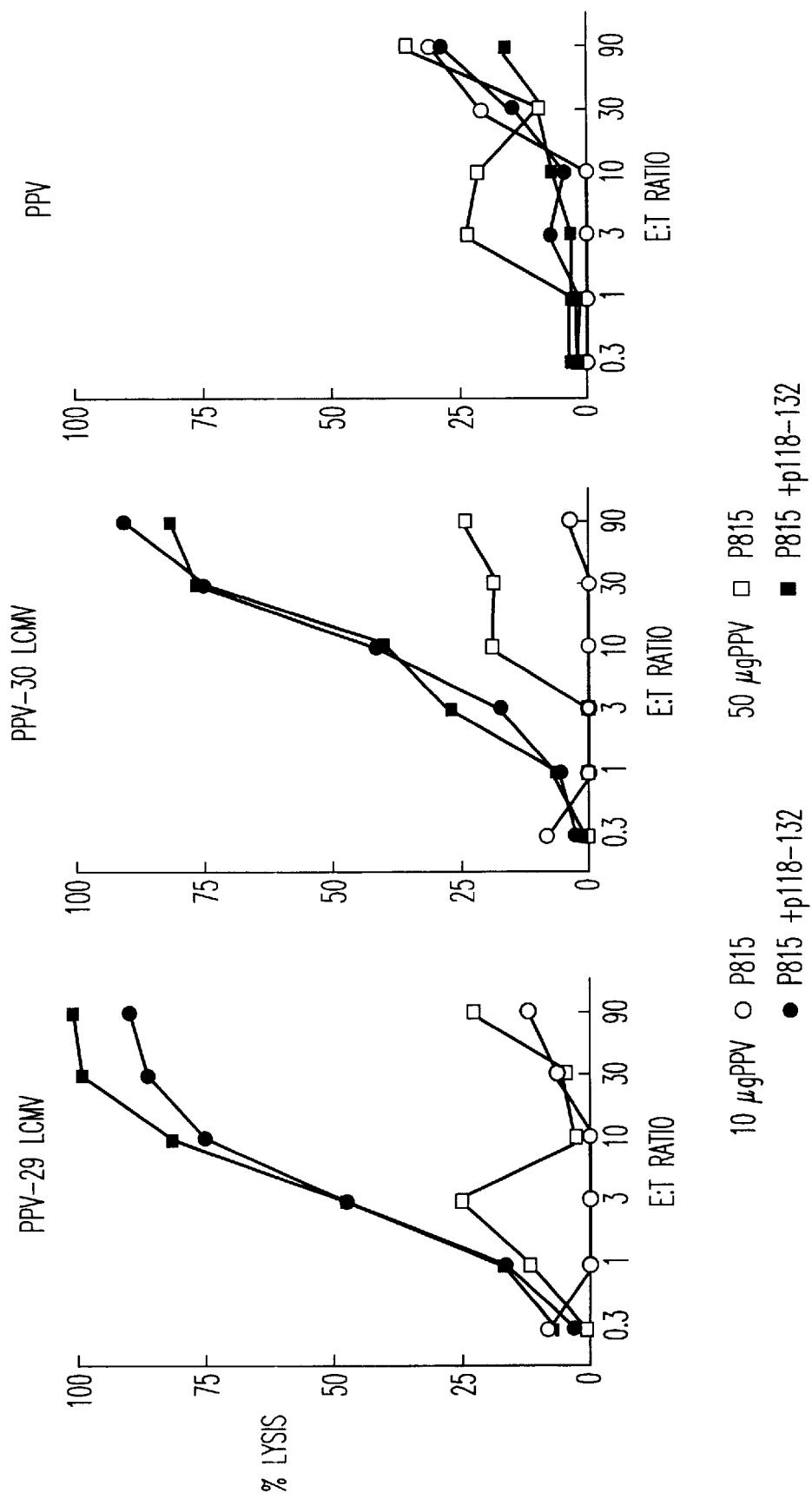

As illustrated in FIG. 1, the vector pPPV29 was obtained by digestion and replacement of the fragment XhoI—NcoI of the vector pPPV17R, originating from the vector pPPV17 described by Martinez et al. (1992, Vaccine, 10, 684–690)., by two PCR amplification products, in order to eliminate a region present in the polycloning site of pPPV17R and the initiation codon of VP2. pPPV17 differed from pPPV17R only in the direction of the VP2 cloned gene compared to the polylinker. All the PCR amplifications were performed in a total volume of 100 μl with one unit of DNA polymerase Vent (New England Biolabs), 10 ng of pPPV17R as matrix, 100 μm of dNTPs and 800 ng of each primer. The amplifications were performed for 25 denaturation cycles at 93° C. for 1 minute, the annealing of the primer being carried out at 50° C. for one minute and the extension at 72° C. for three minutes. The PCR products were cloned in pPPV17R digested by Xho-I and NcoI and dephosphorylated. The ligation mixtures were used to transform E. coli DH5 bacteria. Two plasmids were obtained by this procedure : pPPV29, which contained a single Xho-I cloning site adjacent to the original ATG codon of VP2, and pPPV30 which contained a single Xho-I cloning site, but without the ATG initiation codon.

The pPPV29 mod vector was thus obtained: the VP2 gene was obtained by digestion of pPPV29 by Pst I, then ligated in the PstI cloning site of the pMTL24 plasmid in order to provide the BamHI sites for subcloning in the baculovirus transfer vectors.

Two oligonucleotides coding for the CD8$^+$ antigenic determinant and the initiation codon, and containing two XhoI sites were synthesized. They had the sequences SEQ ID No1 and No2 given below:

SEQ ID No1
5'TCGAGATGCGACCACAAGCTTCAGGAG-TATACATGGGAAAC CTAACAGCACAAC3'

SEQ ID No2
5'TCGAGTTGTGCTGTTAGGTTTCCCATG-TATACTCCTGAAGCT TGTGGTCGCATC3'

These two complementary oligonucleotides were supplied by Medprobe (Norway). They were phosphorylated using polynucleotide kinase T4, annealed at 70° C. for 15 minutes and ligated in the XhoI site of the pPPV29mod plasmid digested by XhoI, which contained the gene coding for PPV-VP2.

*Escherichia coli* DH5 cells were transformed with the ligation mixture and spread onto LB medium containing 100 μg/ml ampicillin (Hanahan, 1983, J. Mol. Biol., 166, 557–580). The recombinants containing the LCMV insert were selected, then sequenced by the dideoxy procedure in order to determine the direction and completeness of the sequences inserted. The recombinant clone containing the LCMV sequence in the correct direction was referred to as pPPV29mod/LCMV.

Preparation of transfer vectors in baculoviruses and selection of recombinant baculoviruses.

The chimeric VP2 sequence was obtained from the pPPV29mod/LCMV vector by digestion by BamHI and subcloned in the single BamHI restriction site of the baculovirus PAcYM1 transfer vector.

The recombinant clones were prepared as described above and analyzed by the plasmid DNA minipreparation method and by restriction mapping. The insertion sequences of the positive clones were sequenced in order to re-verify the completeness of the antigenic determinant inserted and the flanking sequences. Finally, the DNA, purified by phenol, was precipitated by two volumes of ethanol. The recombinant clone thus obtained was named pAcYM1/LCMV/ppv29mod.

To obtain the recombinant baculoviruses, a mixture of 2 μg of purified transfer vector DNA and 500 ng of $AcRP231acz^+$ parental DNA was added to Sf9 insect cells in the presence of DOTAP transfection reagent (Boehringer, Mannheim), according to the manufacturer's instructions. The transfection was continued until the cytopathic effect was complete. After 9 days, the cultures were recovered and the clarified supernatant was used to isolate the recombinant baculovirus plaques according to methods already known in the state of the art and described by Sedlik et al. (J. Gen. Virol., 1995, 76, 2361–2368). The recombinant clones were selected by using their white phenotype (white plaque: recombinant; blue plaque: wild phenotype).

The recombinant baculoviruses were purified until no further blue plaque could be detected. Stocks of viruses having a high titer of recombinant baculovirus AcNPV.PPV-LCMV ($>10^8$) were prepared.

A clone, named AcPP29-LCMV, was deposited on Dec. 20, 1995, at the European Collection of Animal Cell Cultures (ECACC) under the No. V 95122022.

Analysis of recombinant proteins.

The Sf9 cells were infected by the recombinant baculoviruses at an infection level of 1 pfu per cell (one plaque-forming unit per cell) and the cell extracts were collected 72 hours after infection.

Protein dissociation buffer was added to each cell extract, and the mixtures were heated at 100° C. for 5 minutes, then separated on SDS-9% PAGE.

The gels were colored with Coomassie blue or transferred onto nitrocellulose membranes using a semi-dry apparatus, at 22 volts for 30 minutes.

The membranes were incubated with mouse serum directed to the LCMV $CD8^+$ antigenic determinant (dilution 1/1200) for two hours at ambient temperature.

After washing, the fixed antibodies were detected by protein A conjugated to peroxidase (dilution 1/2000) using 4-chloronaphthol as substrate until development of the color. The membranes were then rinsed with distilled water to stop the reaction. After coloration of the SDS gels with Coomassie blue, a visible band at 67 kD was detected in the extracts of the Sf9 cells infected with the recombinant baculoviruses. The size observed corresponded to the size expected for the chimeric VP2-LCMV protein. The identity of this protein was confirmed by immunotransfer. The specific mouse antiserum showed a very clear positive reaction with the 67 kD protein from the infected cell extracts. The intracellular localization of the recombinant protein was analyzed by immunotransfer of the different cell fractions. This showed that the chimeric LCMV-VP2 protein was a soluble cytoplasmic protein.

Purification of the particles.

Sf9 cells were infected with recombinant baculovirus at an infection level of 1 pfu per cell. The cells were collected 72 hours after infection, washed with PBS and lysed by osmotic shock at 4° C. in a 25 mM bicarbonate solution. The cell debris was removed by low-speed centrifugation. The particles contained in the extracts were then purified by precipitation in a saturated solution of 20% ammonium sulfate. The precipitate was centrifuged at 15000 rpm for 15 minutes, resuspended in PBS and dialyzed overnight against the same buffer. The identity and properties of the particles were confirmed by SDS-PAGE, immunotransfer and electron microscopy.

These purified particles were used for immunization and induction of lymphocyte cytotoxicity (CTL).

Immunization of mice.

The mice received an intraperitoneal injection of a composition containing the recombinant viral pseudo-particles according to the invention (PPV-LCMV), or empty (PPV), in the absence of adjuvant. The positive controls were mice subcutaneously injected, at d21, with synthetic peptide 118–126 (supplied by Neosystem, Strasbourg, France) in incomplete Freund's adjuvant (IFA). The negative controls received pseudo-particles not expressing the LCMV antigenic determinant.

Induction of cytotoxic cells.

7 to 14 days after the last immunization, the spleens were removed from the immunized mice. $25\times10^6$ immune cells were cultured, in the presence of $25\times10^6$ irradiated splenocytes from native syngeneic mice, in flasks containing nutrient medium (RPMI 1640, 10% fetal calf serum, glutamine and antibiotic) for 5 days at 37° C., 5% $CO_2$.

The stimulating cells were sensitized in vitro with 0.05 μM synthetic peptide 118–126 or with 0.5 μM synthetic peptide 118–132 (also supplied by Neosystem, Strasbourg, France).

Cytotoxicity test.

The cytotoxic activity of the effector lymphocytes was measured after 5 days. The P815 target cells were preincubated either with nutrient medium (negative control), or with synthetic antigenic peptide and simultaneously labelled with $^{51}Cr$ for 1 h., at 37° C. The effector lymphocytes were then incubated with the labelled cells, at different effector/target ratios (E/T ratio) in nutrient medium in 96 round-bottomed wells plates, for 4 to 5 h., at 37° C. The targets were incubated under the same conditions with medium to measure the spontaneous liberation of the $^{51}$Cr and with 1N hydrochloric acid to measure the maximum liberation of $^{51}$Cr. The activity of the cytotoxic lymphocytes was determined by counting the radioactivity present in the culture supernatants, corresponding to the release of $^{51}$Cr by the lysed target cells.

$$\% \text{ specific lysis} = \frac{\text{experimental cpm} - \text{spontaneous cpm}}{\text{maximum cpm} - \text{spontaneous cpm}}$$

This calculation was performed with the target cells incubated in nutrient medium (P815) and with target cells incubated with synthetic peptide (P815+p118–132), as shown on the graphs of FIGS. 2 to 5.

Results.

As can be seen on studying FIGS. 2 to 5, a single injection of 10 μg of recombinant pseudo-particles presenting the CD8$^+$ T antigenic determinant of LCMV yielded practically 100% of lysis, in other words as much as the positive control synthetic peptide 118–126+IFA, which confirms that the pseudo-particles according to the invention are capable of inducing CTL responses in vivo at a high level without addition of adjuvant.

This induction was specific to the antigenic determinant inserted since no cytotoxic T response was obtained when the mice were immunized with equivalent doses of pseudo-particles not expressing the LCMV antigenic determinant. The cytotoxic T cells thus induced specifically lysed the P815 target cells coated with the peptide corresponding to the inserted antigenic determinant.

Figure 5B:
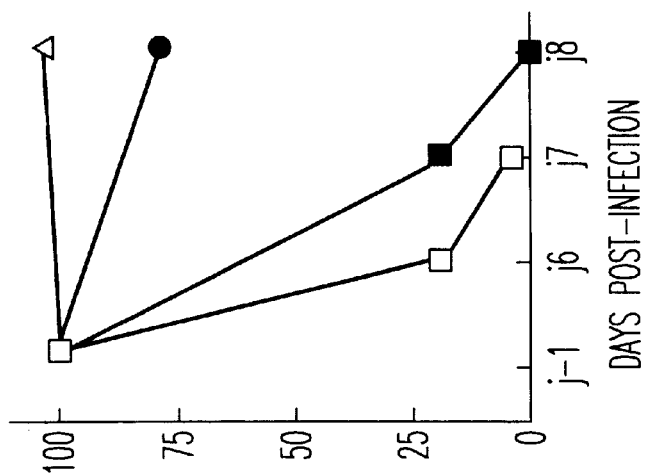
Figure 5A:
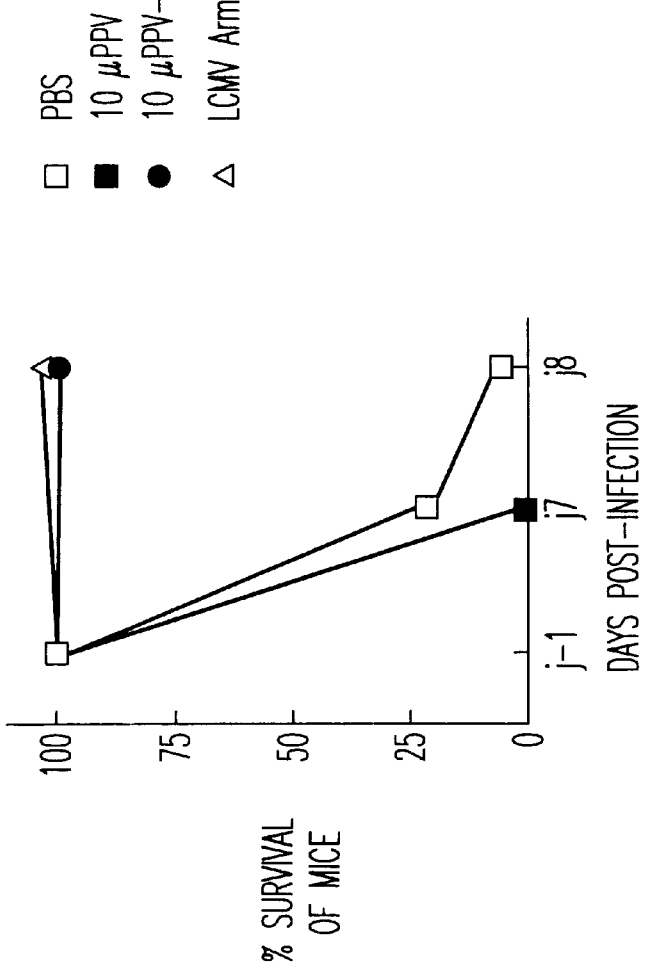

FIG. 5 shows that the mice injected with the pseudo-particles were protected against viral infection at 28 days, and that ⅘ mice were protected at 70 days.

EXAMPLE 2

Induction of specific CD4$^+$ T responses to a hepatitis B antigenic determinant by parvovirus pseudo-particles.

1) Materials and methods

Insertion of the PreS:T antigenic determinant of HBV at the N-terminal end of the PPV VP2 protein.

Two oligonucleotides were synthesized, coding for the PreS:T antigenic determinant of HBV, with the following sequences:

Seq ID No.3:
5'TCGAGATGCAATGGAATTCTACCACCT-TCCACCAAACCCTGCAAC3'

Seq ID No.4:
5'TCGAGTTGCAGGGTTTGGTGGAAGGTGG-TAGAATTCCATTGCATC3'

These two oligonucleotides are complementary and contain two flanking sequences of the XhoI site at the ends in order to allow direct cloning in the pPPV30 vector. The oligonucleotides wee supplied by ISOGEN (Netherlands). They were phosphorylated using polynucleotide kinase T4, annealed at 70° C. for 15 minutes then ligated in the presence of pPPV30 digested by XhoI and treated with phosphatase at 14° C. overnight. The mixture was used to transform *Escherichia coli* (strain DH5) cells.

The colonies were analyzed using EcoRI and HindIII restriction enzymes to verify the presence of the inserted sequences. The recombinants containing the sequence of the antigenic determinant were sequenced to confirm that no change or mutation had taken place during these treatments.

Preparation of a transfer vector of the PreS:T-PPV preparations in baculoviruses and production of recombinant baculoviruses.

The recombinant plasmids containing the PreS:T antigenic determinant in the correct direction were digested using BamHI, and the modified VP2 was subcloned in the pAcYM1 transfer vector (Matsuura et al., 1987, J. Gen. Virol. 68, 1233–1250). The recombinant clones were analyzed as described above and the sequences of the insertions were confirmed by sequencing. The recombinant clone was named pAcYM1/PreS:T-pPPV30.

The recombinant baculoviruses were obtained by transfection of SF9 insect cells, as described in example 1, and stocks of viruses with high titers were prepared (>10$^8$ pfu/ml). The recombinant virus was named AcPPV30-PreS:T.

It was deposited on Aug. 15, 1996, at the European Collection of Animal Cell Cultures (ECACC) under the No. V 96081412.

Analysis and purification of recombinant proteins.

Sf9 cells were infected (Smith et al., 1983, Mol. Cell. Biol., 3, 2156–2165) at an infection level of 1 pfu/cell with the recombinant baculovirus AcPPV30-PreS:T. The infected cells were collected 72 hours after infection and analyzed by electrophoresis on 9% polyacrylamide gels in the presence of SDS, then by immunotransfert. The results showed the presence of modified recombinant VP2 protein.

To purify the chimeric VP2 particles, the infected cells were lysed using 25 mM sodium bicarbonate, the cell debris were removed by centrifugation, and the supernatant containing the particles was precipitated with 20 min., ammonium sulfate for 20% at 4° C. The residue, which had been considerably enriched in VP2 particles, was collected by centrifugation and dialyzed again against PBS overnight. The purified particles were stored at 4° C. until use.

Stimulation of specific T hybridomas of the PreS:T peptide of HBV by pseudo-particles expressing this peptide.

Figure 6A:
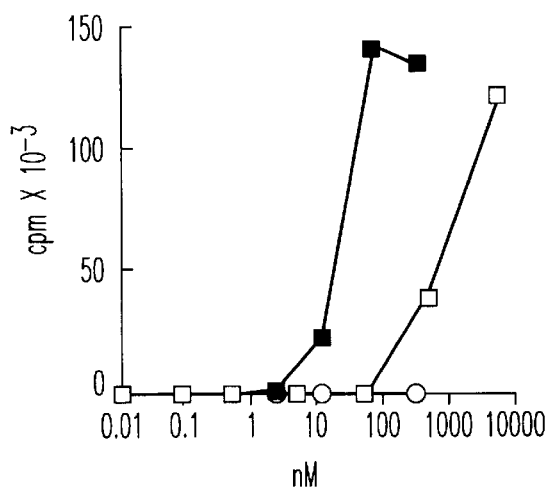
FIGS. 6A to 6D illustrate the stimulation of specific T hybridomas of the CD4+ T PreS:T antigenic determinant of HBV, 51E12 (6A and 6C) or 52A12 (6B and 6D) by B lymphoma cells (6A and 6B) or irradiated splenocytes (6C and 6D) placed in the presence of peptide PreS:T, of PPV-PreS:T recombinant pseudo-particles or of PPV pseudo-particles (VP2).
Figure 6B:
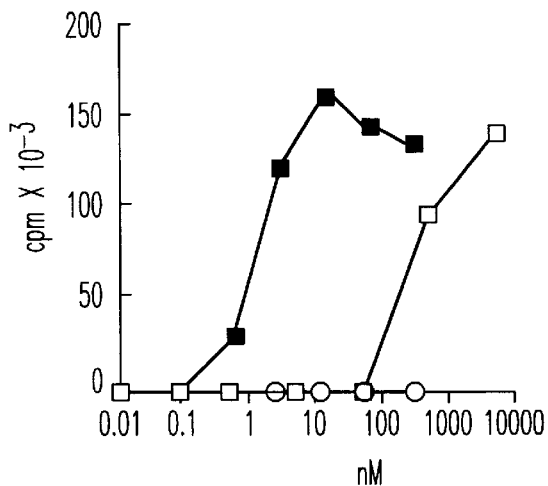
Figure 6C:
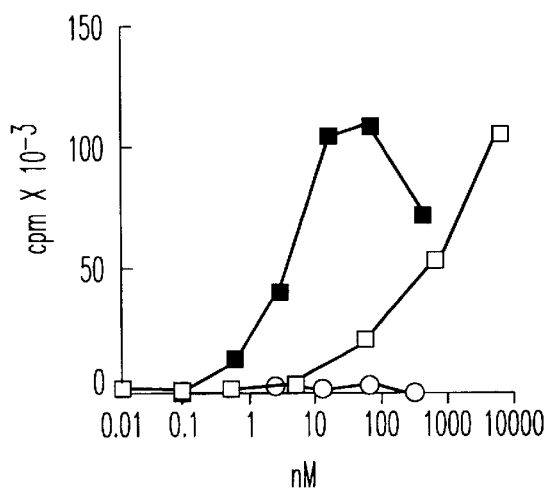
Figure 6D:
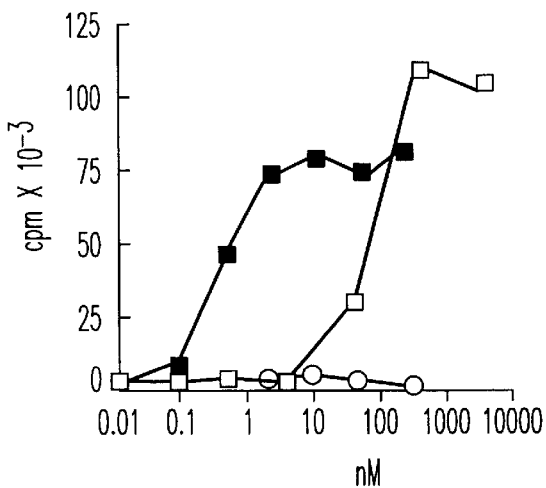

10$^5$ cells of B lymphoma, M12C10(H-2$^{d/q}$) (FIGS. 6A and B) or 5.10$^5$ irradiated splenocytes of DBA/1(H-2$^q$) mice (FIGS. 6C and D) were incubated at 37° C., in the presence of different concentrations of peptide PreS:T corresponding to the sequence 120–132, of PPV-PreS:T recombinant pseudo-particles, or of PPV (VP2) pseudo-particles, then used to stimulate 10$^5$ specific T hybridomas, 51E12 (6A and 6C) or 52A12 (6B and 6D), of the PreS:T peptide and restricted by the molecules I-A$^q$; after 24 hours, the culture supernatants were removed, then dosed with the IL-2 dependent CTLL ligne. Four days later, the proliferation of the CTLL cells was measured by incorporation of tritiated thymidine.

Induction in the absence of adjuvant of specific proliferative responses of the PreS:T peptide of HBV after immunization of mice with viral pseudo-particles of parvovirus expressing this peptide.

Figure 7A:
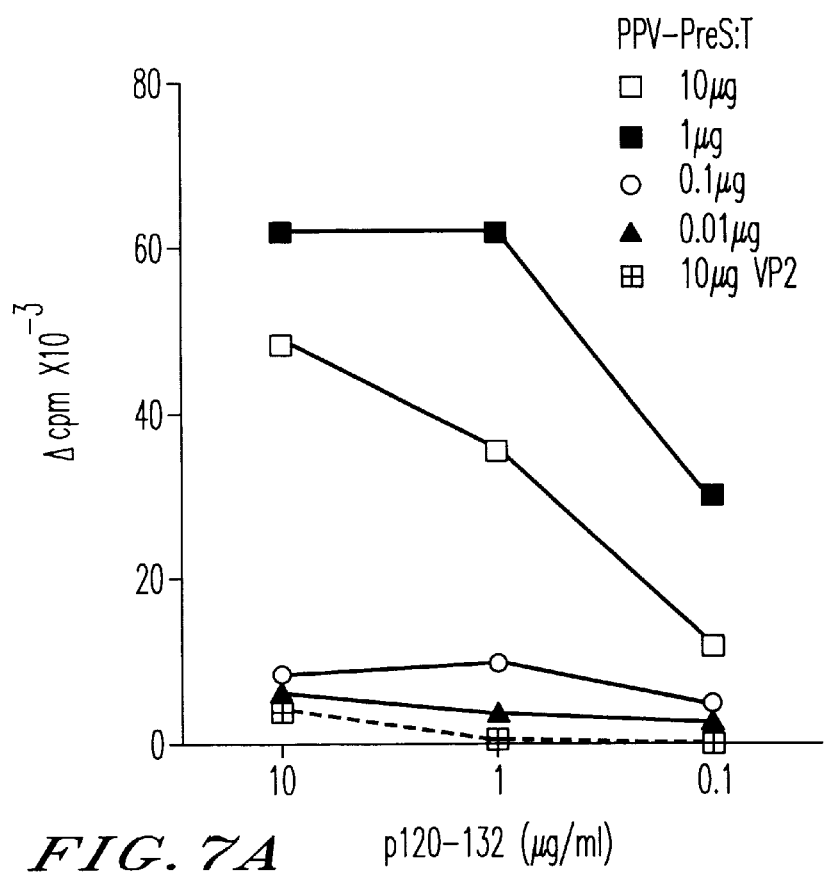
FIGS. 7A and 7B illustrate the proliferative response of ganglion cells stimulated in vitro with peptide PreS:T (FIG. 7A) or PPV (VP2) pseudo-particles (FIG. 7B), said cells being from DBA/1 mice immunized with from 0.01 μg to 10 μg of PPV-PreS:T or 10 μg of PPV (VP2), in the absence of adjuvant.
Figure 7B:
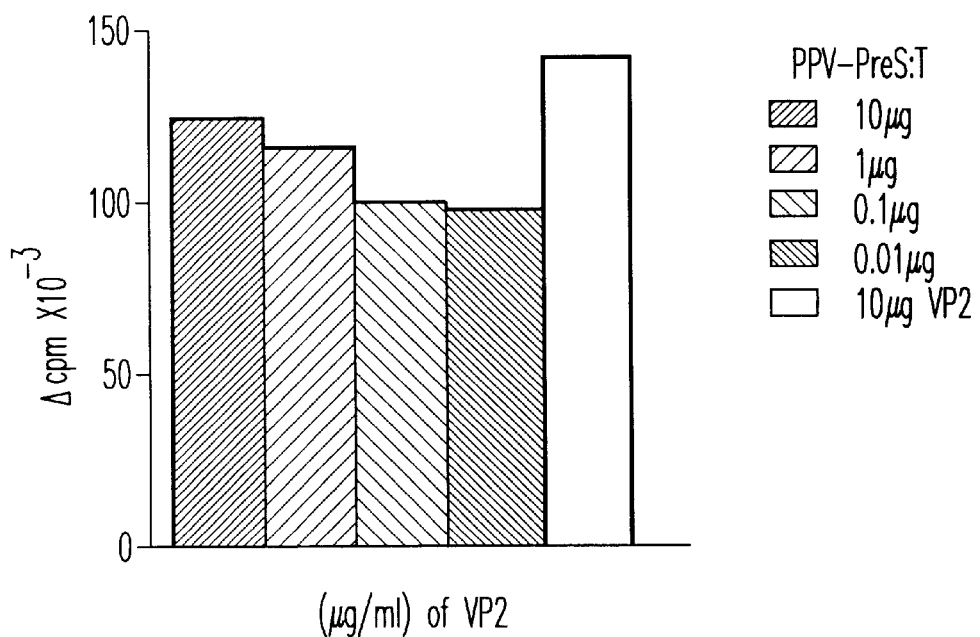

DBA/1 (H-2$^q$) mice were immunized by subcutaneous injection with 10 μg, 1 μg, 0.1 μg or 0.01 μg of PPV-PreS:T recombinant viral pseudo-particles, or 10 μg of PPV (VP2) pseudo-particles. Ten days later, the draining ganglion cells were restimulated in vitro with different concentrations of the PreS:T peptide (FIG. 7A) or with 0.5 μg/ml of PPV (VP2) (FIG. 7B). Three days later, the proliferation of the ganglion cells was measured by incorporation of tritiated thymidine.

Capacity of the PPV-PreS:T recombinant viral pseudo-particles to induce a specific proliferative response of the PreS:T peptide in the presence or absence of adjuvant.

Figure 8A:
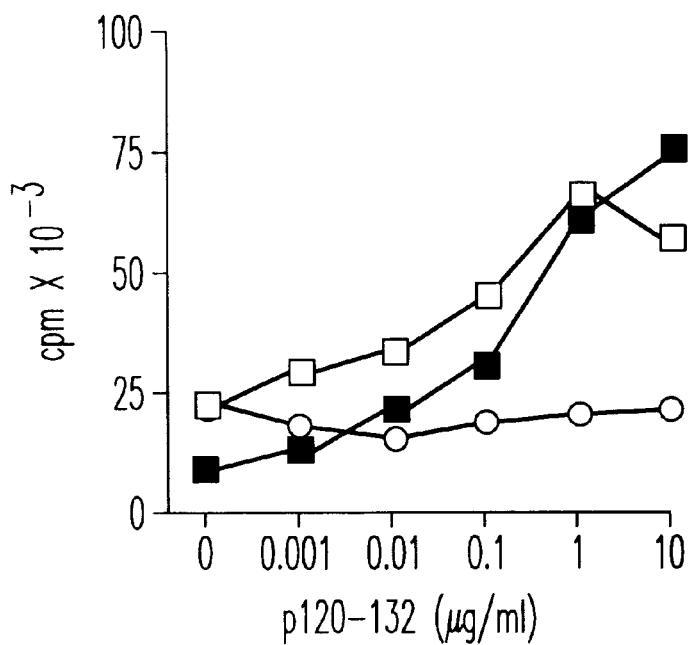
FIGS. 8A and 8B represent the proliferation of ganglion cells from DBA/1 mice immunized with PPV-PreS:T in PBS medium or in the presence of complete Freund's adjuvant or PPV (VP2), restimulated by peptide PreS:T (FIG. 8A) or PPV (VP2) (FIG. 8B).
Figure 8B:
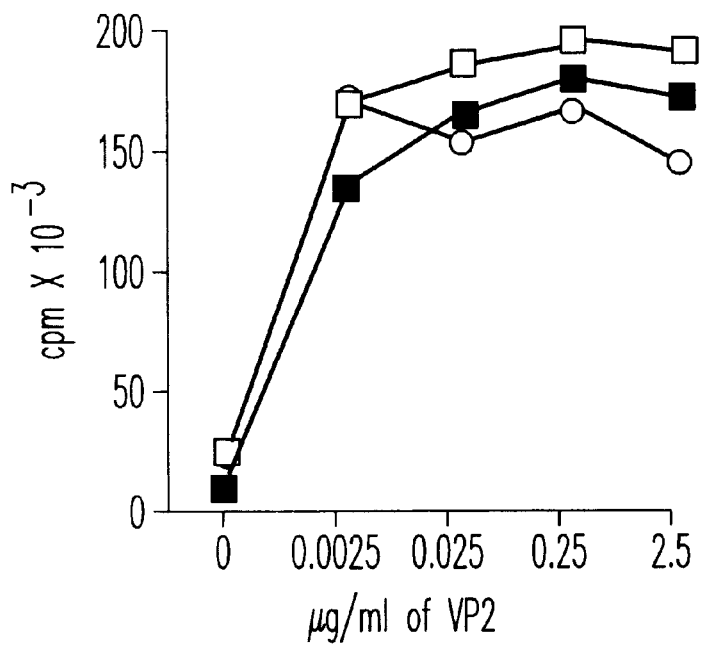

DBA/1 (H-2$^q$) mice were immunized by subcutaneous injection with 10 μg PPV-PreS:T recombinant viral pseudo-particles in saline solution (PBS) or in emulsion with complete Freund's adjuvant (CFA), or with 10 μg of PPV (VP2) pseudo-particles in CFA. Ten days later, the draining ganglion cells were restimulated in vitro with different concentrations of the PreS:T peptide (FIG. 8A) or with PPV (VP2) (FIG. 8B). Four days later, the proliferation of the ganglion cells was measured by incorporation of tritiated thymidine.

2) Results

The CD4+ T PreS:T antigenic determinant located in the PreS2 region (corresponding to the sequence 120–132) of the HBV virus was introduced into the parvovirus VP2 protein as described in example 1. The control PPV (VP2) or PPV-PreS:T recombinant pseudo-particles were purified according to the methods used for the LCMV antigenic determinant in example 1.

The antigenicity of these particles was first analyzed in vitro against PreS:T antigenic determinant specific T hybridomas. As can be seen in FIG. 6, the viral pseudo-particles containing the PreS:T antigenic determinant very strongly stimulated the production of IL-2 by these specific T hybridomas, and in a specific manner in comparison with the control pseudo-particles. If the effectiveness of the PPV-PreS:T is compared to peptide p120–132 on a molar basis, the pseudo-particles are 100 to 1000 times more antigenic than the peptide.

The immunogenicity of these particles was then tested in vivo, either alone at various doses (0.01 to 10 μg) (FIG. 7), or at 10 μg in the presence or absence of complete Freund's adjuvant (FIG. 8). These experiments showed the very strong immunogenicity of the PPV-PreS:T pseudo-particles which, in the absence of any adjuvant and at low doses (a single injection of 1 μg), induced very high proliferative responses against the antigenic determinant inserted (FIG. 7). These responses were as strong when the pseudo-particles were injected alone as when they were administered in the presence of complete Freund's adjuvant (FIG. 8).

EXAMPLE 3

Induction in vivo of a proliferative response by pseudo-particles containing the C3:T antigenic determinant of Poliovirus VP1.

Materials and methods

Antigen

The peptides C3:B (93–103), C3:T (103–116), C3:TB (93–116) of the type 1 protein of poliovirus VP1 were synthesized by Neosystem (Strasbourg, France).

Insertion of the C3:B and C3:T antigenic determinants into the pPPV29 and pPPV30 vectors.

Two pairs of complementary oligonucleotides corresponding to the C3:T and C3:B antigenic determinants, and having the sequences SEQ ID No.5 to SEQ ID No.8 below, were synthesized.

SEQ ID No.5
5'TCGAGATGAAGCTTTTCGCTGTCTGGAA-GATCACCTACAAAGACACCC 3'
SEQ ID No.6
5'CTACTTCGAAAAGCGACAGACCT-TCTAGTGGATGTTTCTGTGGGAGCT 3'
SEQ ID No.7
5'TCGAGATGGACAACCCCGCTAGCACCAC-CAACAAGGACAAAC 3'
SEQ ID No.8
5'CTACCTGTTGGGGCGATCGTGGTGGT-TGTTCCTGTTTGAGCT 3'

The phosphorylated oligonucleotides were mixed and heated to 70° C. for 15 minutes before ligation in the presence of pPPV29 and pPPV30 treated with calf intestinal alkaline phosphatase. The completeness and direction of the antigenic determinant sequences was confirmed by sequencing. In total, four constructions were prepared, two for each antigenic determinant: pPPV29-C3:B, pPPV29-C3:T, pPPV30-C3:B and pPPV30-C3:T.

In order to determine the maximum length of sequence which could be removed without modifying the structure of the capsid, three different constructions were prepared by PCR with progressive length deletions.

Three primers with sequences SEQ ID No.9 to SEQ ID No.11 were synthesized:
SEQ ID No.9
5'GCCTCAACTAGTTGTAGGAATATATTT 3'
SEQ ID No.10
5'CATTTAACTAGTTCTCATTTTTGCTGG 3'
SEQ ID No.11
5'GTTTCAACTAGTTATTATTCTAGGTTG 3'

These primers correspond to nucleotides 4449–4475, 4377–4403 and 4323–4349, respectively. They were synthesized in order to create deletions of 18, 42 and 60 amino acids, respectively. These primers were used in combination with the 5' primer of sequence SEQ ID No.12 below:
SEQ ID No.12
5' TTCCATGGGTGAAAATGTGGAACAACA 3'
contained between positions −4 and 23 of the VP2 gene.

Figure 9:
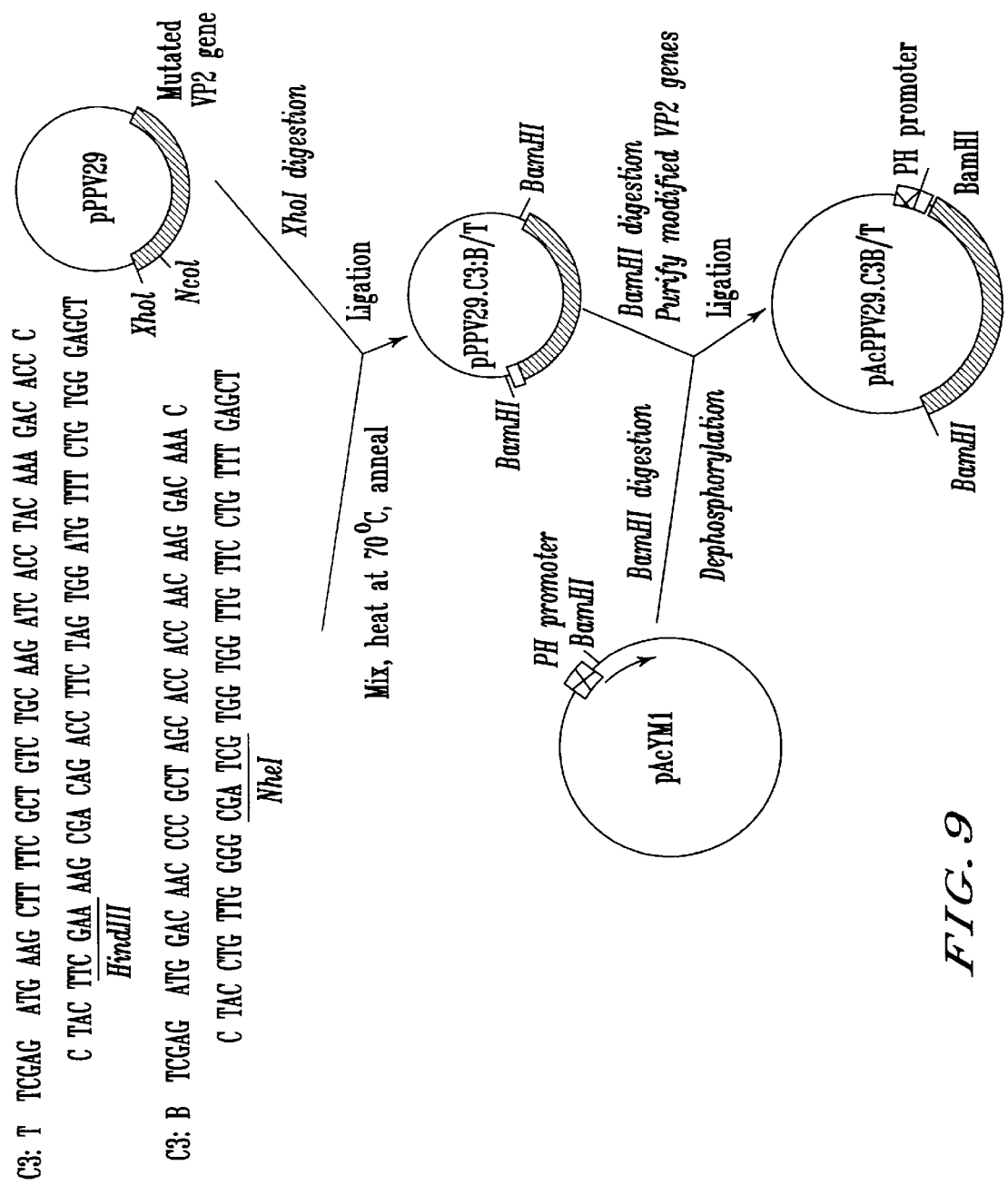
FIG. 9 illustrates the preparation of a transfer vector pAcPPV29.C3B/T from pPPV29 and pAcYM1.

The SpeI sites used for the screening are underlined in FIG. 9. The forms having deletions in VP2 were cloned in the pMTL25 vector treated with alkaline phosphatase and digested by SmaI in order to provide the BamHI sites for the subcloning in the transfer vector towards the baculovirus pAcYM1, then transformed in *Escherichia coli* strain DH5. The recombinant clones were characterized by restriction mapping with SpeI and BamHI and the absence of deleted sequences was confirmed by sequencing. The resulting plasmids were named pPPV VP2/ΔC4475, pPPV VP2/ΔC4403 and pPPV VP2/ΔC4349.

All the recombinant clones containing modified forms of VP2 were digested by BamHI and subcloned in the baculovirus pAcYM1 transfer vector. The recombined transfer vectors derived from pAcYM1 were named pAcPPV29-C3:B, pAcPPV30-C3:B, pAcPPV29-C3:T and pAcPPV30-C3:T. The direction and the sequences between the codons for initiation of translation and the sites of initiation of transcription were determined by sequencing.

The recombinant baculoviruses were obtained by co-transfection of viral DNA of AcRP-23-lacZ linearized by Bsu361 (500 ng) as described by Possee & Howard, 1987 (Nucleic Acid Research, 15, 10233–10248) and the transfer vectors (2 μg) by using the lipofectine technique (Gibco BRL) as described by Felgner et al. (1987, Proceedings of the National Academy of Sciences, USA, 845, 7413–7417). The recombinant viruses were selected by their LacZ-negative phenotype and purified on plates before the preparation of stocks with high titers.

Four recombinant baculoviruses, AcPPV29-C3:B, AcPPV30-C3:B, AcPPV29-C3:T and AcPPV30-C3:T were prepared. Cells of *Spodoptera frugiperda* were infected with an infection level of 1 pfu per cell with a recombinant baculovirus expressing one of the PPV VP2 hybrid proteins. The cells were collected 72 hours after infection, washed in PBS, lysed with NaHCO$_3$ (25 mM), pH 9.5, at a density of 5×10$^6$ cells per ml, and mixed with equal volumes of SDS buffer. Samples were boiled for 5 minutes before being loaded onto 9% polyacrylamide-SDS gels. For the immunohybridization analyses, the proteins were transferred onto a nitrocellulose membrane using a semi-dry system (Bio Rad). The hybridizations were labelled using anti-PPV polyclonal serum (gift from Doctor K. Dalsgaard, State Veterinary Institute for Virus Research, Lindholm, Denmark) to confirm the presence of the VP2 gene product, with an anti-C3:B monoclonal antibody (gift from Doctor Crainic, Institut Pasteur, Paris, France) and with a mouse anti-C3:T polyclonal antibody to verify the expression of these antigenic determinants.

The bound antibodies were detected using immunoglobulins G conjugated with alkaline phosphatase (Sigma) and nitric tetrazolium blue (Gibco BRL) as substrate.

The highest expression level was observed for the recombinant AcPPV30-C3:B. The lowest expression was observed for AcPPV29-C3:T and AcPPV30-C3:T. No expression was detected for the clone AcPPV29-C3:B.

The recombinant baculoviruses AcPPV30-C3:B and AcPPV29-C3:T were selected.

In order to purify the particles, cytoplasmic extracts of the cells lysed by bicarbonate were precipitated with 25% ammonium sulfate. The pellets, containing the majority of the VP2 proteins, were resuspended in PBS and filtered through a Sephadex G50–80 column.

Determination of the specific proliferative response of the antigens.

BALB/c mice were immunized subcutaneously or intraperitoneally, and 14 days later, the inguinal lymphatic ganglions or spleen were removed. A cell suspension was prepared in RPMI complemented with 0.5% normal mouse serum, 1.5% FCS, 2 mM glutamine, 50 µM 2-mercaptoethanol and antibiotics. $8 \times 10^5$ cells were incubated with different doses of peptide in microculture plates, with a final volume of 0.2 ml. Each test was carried out 3 times. The cell proliferation was measured by the incorporation of tritiated thymidine during the final eighteen hours of the 4th day of culture. The radioactivity incorporated was measured in a scintillation counter. The results are expressed as the mean value of three cultures.

Results

Induction of the T cellular proliferative response by PPV-C3:T Pseudo-particles.

The capacity of pseudo-particles expressing the C3:B or C3:T antigenic determinants to induce a T response against the inserted peptides was analyzed in BALB/c (H-2$^d$) mice. In a first series of experiments, the BALB/c mice were injected subcutaneously with 10 µg of PPV-C3:T or PPV-C3:B (as negative control) pseudo-particles in CFA, while a control group received 10 µg of synthetic C3:T peptide in CFA.

After two weeks, the lymphatic ganglion cells were stimulated in vitro with different doses of C3:T peptide. The results of this experiment (FIG. 10A) clearly show that the subcutaneous immunization with PPV-C3:T hybrid particles in CFA induced a good proliferative response specific to the peptide. This response was clearly specific, since the lymphatic ganglion cells of mice injected with PPV-C3:B pseudo-particles, or empty PPV pseudo-particles, did not respond to in vitro stimulation with the C3:T peptide.

In a second series of experiments, the PPV-C3:T or PPV-C3:B pseudo-particles in aluminum hydroxide were injected intraperitoneally into BALB/c mice and their spleen cells were stimulated in vitro with C3:T peptide (FIG. 10B). In these conditions the PPV-C3:T pseudo-particles injected with aluminum hydroxide were able to stimulate in vivo the response of spleen cells to the peptide. In contrast, the control PPV-C3:B or empty PPV particles did not induce this specific proliferative response to the peptide.

In general, these results show that the recombinant PPV pseudo-particles are effectively processed by the antigen-presenting cells and thus stimulate T cellular responses against foreign T antigenic determinants.

EXAMPLE 4

Preparation of pseudo-particles containing several antigenic determinants.

Two oligonucleotides with complementary sequences, SEQ ID No.13 and SEQ ID No.14 were prepared:

SEQ ID No.13 (Mut 1+):

5' TCGAGATGTTCGAACAAAACACCGCTCAACCCC 3'

SEQ ID No.14 (Mut 1):

5' TCGAGGGGTTGAGCGGTGTTTTGTTCGAACATC 3'

The 5' ends of each of these oligonucleotides can bind together so as to generate several copies of the antigenic determinant. The oligonucleotides were phosphorylated, then mixed and heated to 70° C. for 15 minutes before ligation in the pPPV29mod plasmid treated with calf intestinal alkaline phosphatase, and digested by XhoI.

The ligation mixtures were used to transform E. coli DH5α bacteria. The recombinant clones were characterized by the use of restriction enzymes. The incorporation of one or more copies, or the absence of incorporation of the Mut1 antigenic determinant, was detected by the determination of the size of the BamHI/HindIII fragment. The completeness of the sequences of the antigenic determinant and their direction were confirmed by sequencing. The modified VP2 genes containing the insertions of the Mut1 antigenic determinant were digested by BamHI and subcloned in the baculovirus pAcYM1 transfer vector.

The recombinant baculoviruses were obtained from co-transfections of 500 ng of AcRP23-lacZ viral DNA linearized by Bsu361 and 2 µg of individual transfer vectors using the lipofectine treatment described by Felgner et al. (1987, Proceedings of the National Academy of Sciences, USA, 84, 7413–7417).

The recombinant viruses were selected by their LacZ-negative phenotypes and purified on plates before the preparation of viral stocks with high titers for each of the recombinant viruses.

What is claimed is:

1. A recombinant viral pseudo-particle, having a size of between 20 and 60 nm and an icosahedral structure,
   wherein the pseudo-particle is produced by auto-assembly of at least one VP2 structural protein of a parvovirus selected from the group consisting of porcine parvovirus (PPV), canine parvovirus (CPV), feline panleukopenia virus (FPLV), and mink enteritis virus (MEV),
   wherein at least one peptide containing a sequence of 8 to 25 amino acids and comprising at least one T helper cell epitope or CTL epitope is inserted into the N-terminal end of the VP2 protein,
   wherein the epitope is capable of associating with at least one class I and/or II molecule of the major histocompatibility complex (MHC), wherein the association between the epitope and the class I and/or II molecule of the major histocompatibility complex is capable of being recognized by cytotoxic $CD8^+$ and/or $CD4^+$ T lymphocytes and capable of stimulating the induction of a cytotoxic T lymphocytes (CTL) response or a T helper response specific to the epitope.

2. The pseudo-particle of claim 1, wherein the epitope comprises a sequence of 8 to 9 amino acids capable of associating with at least one class I MHC molecule.

3. The pseudo-particle of claim 1, wherein the epitope is an antigenic determinant of the nucleoprotein (NP) of lymphocytic choriomeningitis virus (LCMV).

4. The pseudo-particles of claim 3, wherein the peptide consists of amino acids 118–132 of lymphocytic chloriomeningitis virus (LCMV) nucleoprotein (NP).

5. The pseudo-particle of claim 1, which comprises a combination of multicopies of $CD4^+$ or $CD8^+T$ epitopes.

6. The pseudo-particle of claim 1, wherein the parvovirus is porcine parvovirus (PPV).

7. The pseudo-particle of claim 1, wherein the parvovirus is canine parvovirus (CPV).

8. The pseudo-particle of claim 1, wherein the parvovirus is feline panleukopenia virus (FPLV).

9. The pseudo-particle of claim 1, wherein the parvovirus is mink enteritis virus (MEV).

10. A method of preparing the pseudo-particle of claim 1, comprising:

a) preparing recombinant baculoviruses containing an insert comprising a DNA sequence containing the nucleotide sequence coding for said at least one VP2 structural protein, and a nucleotide sequence coding for said at least one peptide;

b) infecting suitable cell lines with the recombinant baculoviruses of step a) under conditions which allow protein expression; and c) recovering the pseudo-particle from the cell lines.

11. A composition comprising the pseudo-particle of claim 1 and a physiologically acceptable excipient and/or diluent.

12. The composition of claim 11, which does not contain an immunostimulant adjuvant.

13. A recombinant viral pseudo-particle comprising at least one porcine parvovirus (PPV) VP2 structural protein in which at least one CTL epitope consisting of a sequence of 8 to 25 amino acid residues is inserted into the N-terminal end of the PPV VP2 structural protein, wherein the epitope is capable of associating with class I major histocompatibility complex (MHC) molecules and cytotoxic $CD8^+$ T lymphocytes recognize the epitope when associated class I MHC molecules and said association is capable of stimulating the induction of a cytotoxic T lymphocytes (CTL) response specific to the epitope; and the pseudo-particle has an icosahedral structure and a diameter of 20 to 60 nm.

14. A recombinant viral pseudo-particle comprising at least one porcine parvovirus (PPV) VP2 structural protein in which at least one CTL epitope consisting of amino acids 118–132 of lymphocytic choriomeningitis virus (LCMV) nucleoprotein (NP) is inserted into the N-terminal end of the PPV VP2 structural protein, wherein the epitope is capable of associating with class I major histocompatibility complex (MHC) molecules and cytotoxic $CD8^+$ T lymphocytes recognize the epitope when associated class I MHC molecules and said association is capable of stimulating the induction of a cytotoxic T lymphocytes (CTL) response specific to the epitope; and the pseudo-particle has an icosahedral structure and a diameter of 20 to 60 nm.

* * * * *

UNITED STATES PATENT AND TRADEMARK OFFICE
CERTIFICATE OF CORRECTION

PATENT NO.     : 6,458,362 B1
DATED          : October 1, 2002
INVENTOR(S)    : Casal et al.

It is certified that error appears in the above-identified patent and that said Letters Patent is hereby corrected as shown below:

<u>Title page, Item [54] and Column 1, lines 1-3,</u>
Title should read -- [54] RECOMBINANT VP2 PARAVIRAL PSEUDO-PARTICLES ENCODING CTL OR T-HELPER CELL EPITOPES --

Signed and Sealed this

Fourth Day of February, 2003

JAMES E. ROGAN
*Director of the United States Patent and Trademark Office*